United States Patent [19]

Perdue

[11] Patent Number: 5,550,537
[45] Date of Patent: Aug. 27, 1996

[54] APPARATUS AND METHOD FOR MEASURING MASS FLOW RATE OF A MOVING MEDIUM

[75] Inventor: Kenneth L. Perdue, Greenwood, Ind.

[73] Assignee: Endress + Hauser, Inc., Greenwood, Ind.

[21] Appl. No.: 239,330

[22] Filed: May 6, 1994

[51] Int. Cl.[6] .................................................. G08C 19/16
[52] U.S. Cl. .......................... 340/870.01; 340/870.3; 340/870.4; 340/870.16; 324/642; 73/861.04
[58] Field of Search ................... 340/870.01, 870.04, 340/870.05, 870.18, 870.19, 870.26, 870.3, 870.4, 870.16, 606; 324/637, 642; 364/510; 73/861.04, 861, 861.08; 342/22

[56] References Cited

U.S. PATENT DOCUMENTS

| | | | |
|---|---|---|---|
| 3,680,375 | 8/1972 | Joy et al. | 73/194 B |
| 3,762,221 | 10/1973 | Coulthard | 73/861.06 |
| 3,939,406 | 2/1976 | Billeter et al. | 324/636 |
| 4,167,736 | 9/1979 | Tomlinson | 342/22 |
| 4,334,543 | 6/1982 | Fehr | 128/661.09 |
| 4,397,191 | 8/1983 | Forden | 73/195 |
| 4,423,623 | 1/1984 | Ho et al. | 73/61.41 |
| 4,708,021 | 11/1987 | Braun et al. | 73/861.06 |
| 4,726,225 | 2/1988 | Brace et al. | 73/204.23 |
| 4,888,547 | 12/1989 | McGinn et al. | 73/861 |
| 4,976,154 | 12/1990 | Schneider et al. | 73/861.06 |
| 5,025,160 | 6/1991 | Watt | 250/356.1 |
| 5,065,764 | 11/1991 | Nakamura et al. | 128/661.09 |
| 5,198,989 | 3/1993 | Petroff | 364/510 |

Primary Examiner—John K. Peng
Assistant Examiner—Andrew Hill
Attorney, Agent, or Firm—Barnes & Thornburg

[57] ABSTRACT

A mass flow meter is provided for measuring the mass flow rate of a material moving along a flow path. The mass flow meter generates a field of electromagnetic energy through which a material moving along the flow path passes. The mass flow meter includes a receiver that detects an amount of electromagnetic energy reflected from the material which is proportional to the concentration of material moving along the flow path. The amount of electromagnetic energy reflected and an assumed velocity are used to generate a response related to the mass flow rate of the material moving along the flow path.

35 Claims, 21 Drawing Sheets

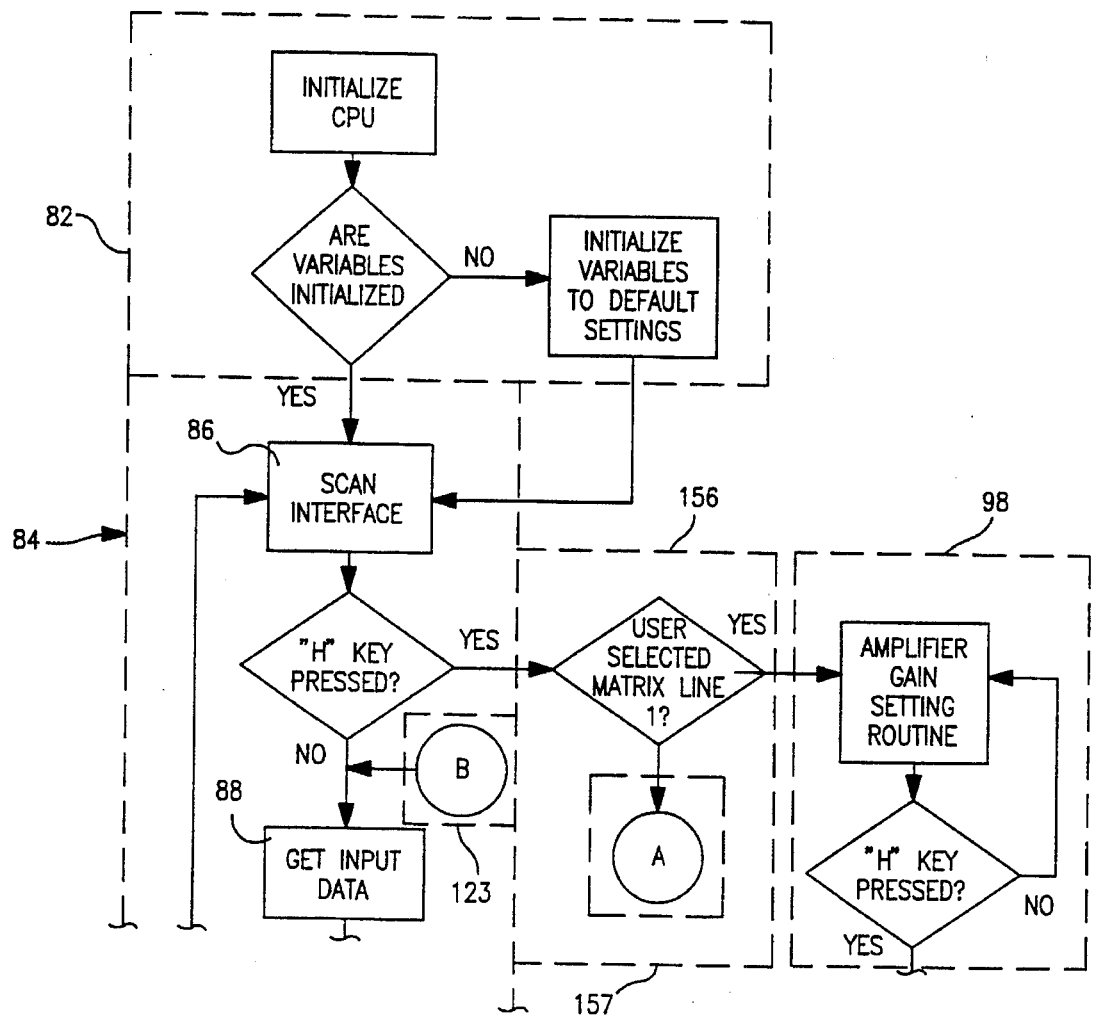
FIG. 6A-I

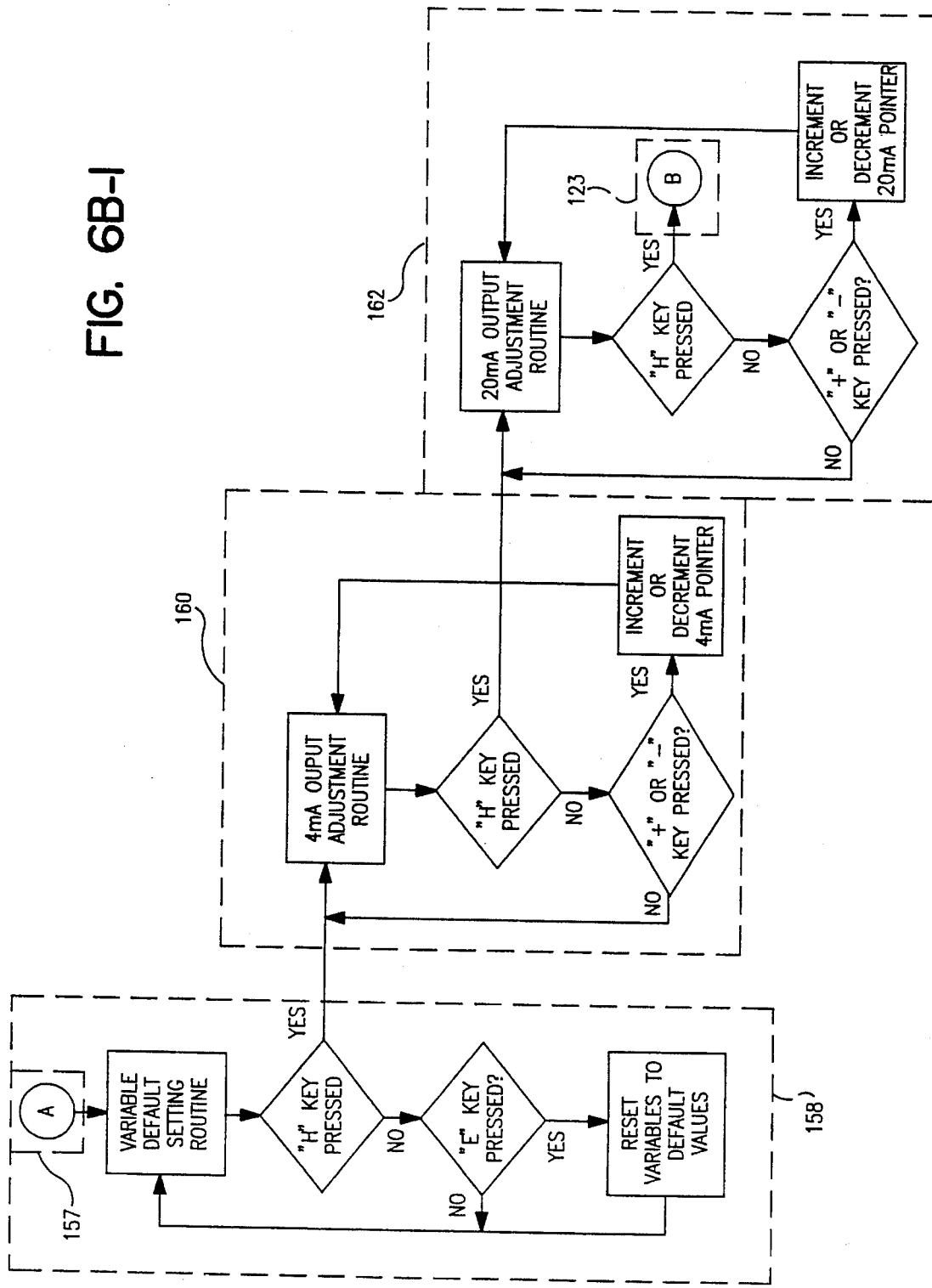
FIG. 6B-I

| Step | Keypad | Action | Result |
|---|---|---|---|
| 1 | H | Press "H" 1 time from RUN mode. Set process flow to the maximum possible (100% recommended). | ![icons] 1 2 |
| | Turnpots | | |
| 2 | Coarse Adjust<br>IV<br>III<br>II<br>I | Adjust coarse knob to increase or decrease amplification until red LED'S are lit for % of process flow. (each LED lit = 10%)<br>Attention<br>Amplification LED will flash if adjusted past the maximum allowable gain setting of the amplifier. | Run<br>0%    50%    100% |
| 3 | Fine Adjust | Adjust fine potentiometer to fine tune amplificcation. | |
| | Keypad | | |
| 4 | H | Press "H" once to continue onto next parameter or 5 times to return to RUN mode. | ![icons] 1 2 |

73

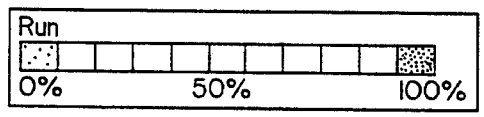
← 73

Example

Process maximum flow is only 90%. Adjust coarse knob until chain LED reaches 90%. Adjust fine potentiometer as needed.

 LED ON      LED ON
    LED FLASHING     LED OFF
    LED OFF     GREEN RUN LED ON

FIG. 7a

| Step | Keypad | Action | Result |
|---|---|---|---|
| 1 | H | Press "H" 2 times from RUN mode. | |
| 2 | −, +, E | Establish zero point calibration. Note: "0" calibration point (no process flow) chould be set first. Press "E" key once. LED flashes for approximately 5 seconds. Zero point accepted, LED is ON. | 73 |
| 3 | −, + | Press "+" or "−" keys to select a new calibration factor point. Each LED lit on chain LED represents 10% of output/display. NOTE: Increase/decrease process flow to the % flow rate for each point required. | Run 0% 50% 100% |
| 4 | E | Press "E" key once. LED flashes for approximately 5 seconds. New pont accepted, LED is ON. For each additional calibration point, repeat steps 3 and 4. | |
| 5 | H | Press "H" key to select another function or press 4 times to return to RUN mode. | |

Attention: It is recommended to establish a zero point plus three additional calibration points(20%, 50%, 80%).

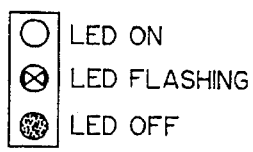 LED ON / LED FLASHING / LED OFF

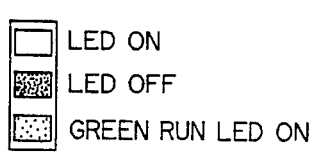 LED ON / LED OFF / GREEN RUN LED ON

FIG. 7b

| Step | Keypad | Action | Result |
|---|---|---|---|
| 1 | H | Press "H" 3 times from RUN mode. | 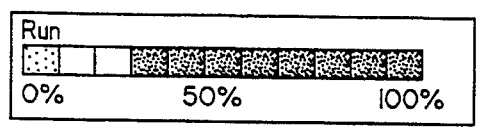 1 2 |
| 2 | ▽ △/+ | Press "+" or "-" keys to increase or decrease time.<br>NOTE: Each LED lit on chain LED is equal to 1 second delay. | Run<br>0%  50%  100% |
| 3 | H | Press "H" key once if relay(s) are to be set. Press 3 times to return to RUN mode. | 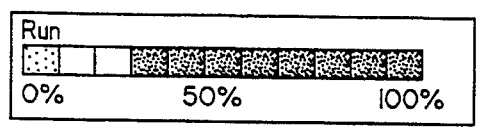 1 2 |

73

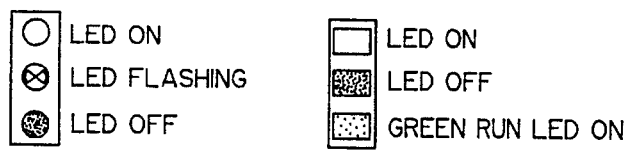

73

Example

Damping setting shown is approximately 3 seconds. The default time is 1 second.

○ LED ON  ☐ LED ON
⊗ LED FLASHING  ▓ LED OFF
● LED OFF  ░ GREEN RUN LED ON

FIG. 7c

| Step | Keypad | Action | Result |
|---|---|---|---|
| 1 | H | Press "H" 4 times from RUN mode. | (icons) 1 2 |
| 2 | −/+ | Press "+" or "−" keys to select % of flow for low setpoint. Minimum setpint is 10%. (see example below) | Run bar 0% 50% 100% |
| 3 | H | Press "H" once more for relay 2. (5 times from RUN mode) | (icons) 1 2 |
| 4 | −/+ | Press "+" or "−" keys to select % of flow for high setpoint. Maximum setpoint is 90%. (see example below) | Run bar 0% 50% 100% |
| 5 | H | Press "H" key once to return to the RUN mode. | (icons) 1 2 |

NOTE: Lo/Hi relay settings must be at least 20% apart.

⊗ = Relay has energized and is functioning.

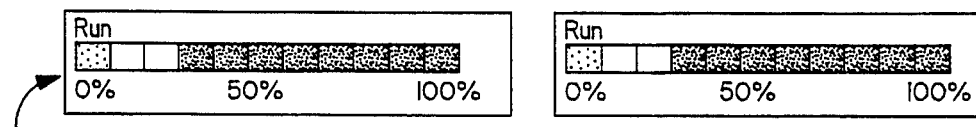

Example
Relay #1 setting shown is 20% (low setting)

Example
Relay #2 setting shown is 80% (high setting)

○ LED ON
⊗ LED FLASHING
● LED OFF

□ LED ON
▓ LED OFF
▒ GREEN RUN LED ON

FIG. 7d

APPARATUS AND METHOD FOR MEASURING MASS FLOW RATE OF A MOVING MEDIUM

BACKGROUND AND SUMMARY OF THE INVENTION

The present invention relates to an arrangement for the contactless measurement of the concentration and the derivation of a mass flow rate of a moving material. More particularly, the present invention relates to an arrangement for the contactless measurement of a mass flow rate of a material moving through an electromagnetic field of known frequency and power based upon the magnitude of the electromagnetic energy reflected by the material as it passes through the field and the velocity of the material.

Disturbance sensors that utilize an electromagnetic signal of known frequency to determine the velocity, distance, or presence of a moving target object are known. Examples of some more well known disturbance sensors include those used in police and aircraft radars. These sensors rely on a change or shift between the frequency of an electromagnetic signal transmitted from the sensor and the frequency of that portion of the signal which is reflected by the moving target object. This change or shift in the frequency of a transmitted and reflected electromagnetic signal is referred to as a Doppler shift. An example of such a change or shift that is detectable at audible frequencies occurs when an audible source is active and moving relative to a person. The sound pitch is perceived to increase when the audible source is moving toward the person and to decrease when the audible source is moving away from the person. The magnitude of this frequency shift or change is proportional to the velocity of the moving object.

The present invention establishes that the concentration of a moving material can be measured based upon the amount of electromagnetic energy or power reflected by the material when it passes through a field of electromagnetic energy of known power. Applicant has observed that as the concentration of a material increases, the magnitude of electromagnetic energy that is reflected by the material also increases. The present invention further establishes that the flow rate of a material moving past a point can be determined by multiplying the mass of the material moving past the point by the velocity of the material. The mass, in turn, is equal to the volume of the material and air illuminated by the field divided by the concentration of the material.

The present invention combines the magnitude of electromagnetic energy reflected from a moving material with the Doppler shift frequency to produce a response related to the mass flow rate of the material. The invention subsequently utilizes this response along with user-supplied data relating to a particular material process flow to generate a linearized response related to the mass flow rate of the material.

Current mass flow rate meters that have sensors, such as antennas and impact plates, which are placed in a material process flow path have several disadvantages. Over time, material can build up on these intrusive sensors which impairs meter sensitivity. Also, such sensors require frequent adjustment because continual and repeated material impact eventually moves them out of calibration. In addition, moving material can impact an intrusive sensor in such a way that it is damaged and in need of repair or replacement. Furthermore, intrusive sensors are subject to changes in ambient conditions within a material process flow, such as temperature and humidity, which requires that a meter be recalibrated to the new ambient conditions or that the conditions of the material process flow be carefully monitored and adjusted. Finally, impact sensors can damage the material in a process flow.

The present invention addresses the above-described problems associated with intrusive mass flow rate meters by providing a contactless (i.e., non-intrusive) mass flow rate meter. The contactless mass flow meter of the present invention includes a transceiver that transmits an electromagnetic signal of known frequency and power across a material process flow. The transceiver detects the magnitude and Doppler shift of the electromagnetic signal that is reflected by material moving along the process flow as it passes through an electromagnetic field established by the signal. The transceiver then combines the magnitude of the reflected electromagnetic signal along with the Doppler shift between the frequency of the transmitted and reflected electromagnetic signals to generate an output signal related to the mass flow rate of the material. This signal has a magnitude substantially equal to the magnitude of the reflected electromagnetic energy and a frequency substantially equal to the difference between the frequency of the transmitted and reflected electromagnetic signals. This signal may be linear or non-linear.

The present invention further includes an amplifier electrically associated with the transceiver to amplify the transceiver output signal to a predetermined level for a predetermined frequency range so that the signal may be further processed. A user interface of the present invention allows the mass flow meter to be set up and calibrated for a particular material process flow as well as adjusted over time. A central processing unit of the present invention calculates a linearized output signal representative of the mass flow rate of the material, which is based upon the user supplied set-up, calibration, and adjustment data and the amplified transceiver output signal. The central processing unit then converts this linearized signal into a digital representation of the mass flow rate of the material. Circuitry of the present invention processes the digital central processing unit output signal to generate a signal related to the mass flow rate of the material.

In a preferred embodiment of the present invention, the digital central processing unit output signal is a pulse width modulated signal. The pulse width of this signal is related to the mass flow rate of the material such that the width of the signal increases with increased material flow rate. A circuit of this preferred embodiment converts the pulse width modulated signal into an analog current signal that is substantially linear through the range of mass flow rates. The magnitude of this current signal is related to the pulse width modulated signal such that the larger the width of the pulse, the higher the magnitude of the current signal.

In the same preferred embodiment, the central processing unit generates two output signals, one of which is indicative of the condition where the mass flow rate is below a user predefined minimum level and the other of which is indicative of the condition where the mass flow rate is above a user predefined maximum level.

The above-described user interface of the present invention allows the mass flow meter to be calibrated to the particular characteristics of a material process flow. The user interface of a preferred embodiment allows the amplification or sensitivity of the meter to be adjusted for a particular material process flow so that optimum amplifier gain occurs during maximum flow rate of the material. To achieve optimum gain, the gain of the amplifier may have to be adjusted up or down depending upon the characteristics of a particular process flow. The user interface of this preferred embodiment also allows calibration points to be set at various material flow rates so that the central processing unit can linearize the amplified transceiver output signal using interpolation techniques. The user interface of this preferred embodiment further allows a user to adjust the size of a central processing unit buffer that receives and stores amplified transceiver output process flow signals. Increasing the size of this buffer increases the number of amplified transceiver output process flow signals that are used by the central processing unit to generate a linearized signal representative of the mass flow rate of the material. The user interface of this preferred embodiment also allows the above-described minimum and maximum mass flow rates to be set and changed for those embodiments of the meter of the present invention which generate these signals. Finally, the user interface provides status information that allows a process flow to be monitored.

Other objects, advantages and novel features of the present invention will become apparent from the following detailed description of the invention when considered in conjunction with the accompanying drawings.

BRIEF DESCRIPTION OF THE DRAWINGS

FIGS. 7a–7d show preferred embodiments of a keypad/control panel of a user interface of the present invention used to set up, calibrate, and adjust the mass flow rate meter of the present invention for different material process flows.

DETAILED DESCRIPTION OF THE DRAWINGS

The present invention establishes that the concentration of a material can be measured based upon the magnitude of electromagnetic energy or power reflected from a material when passing through a field of electromagnetic energy of known power. The power reflected from a target material can be approximated by the following expression:

$$P_R = P_0 + 2G_{Ant} + G_T - S^2$$

where $P_R$=Power reflected from the material $P_0$=Transmitted power $G_{Ant}$=Antenna gain $G_T$=Equivalent target gain S=2 way propagation loss in free space The power reflected from a material "$P_R$" increases with the equivalent target gain "$G_T$", assuming all other factors in the equation are constant. The equivalent target gain "$G_T$" is directly dependent upon the reflectivity and cross-sectional area of the target material. For a given material, the cross-sectional area increases with increased material concentration. Therefore, the reflected power increases with increased material concentration. This relationship is illustrated in FIGS. 1a–1c.

Figure 1A:
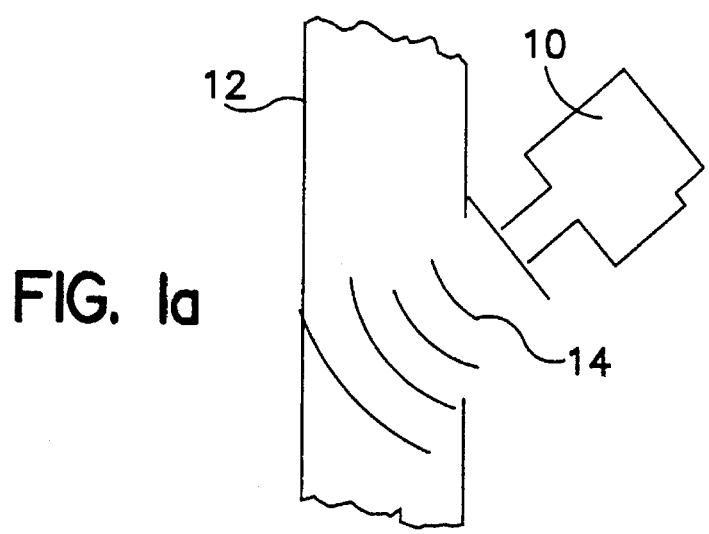
FIGS. 1a–1c illustrate a mass flow rate meter of the present invention transmitting an energy signal across a material flow path and receiving electrical magnetic energy which is reflected by material moving in the flow path, the quantity of which is shown increasing with increased material concentration.
Figure 1B:
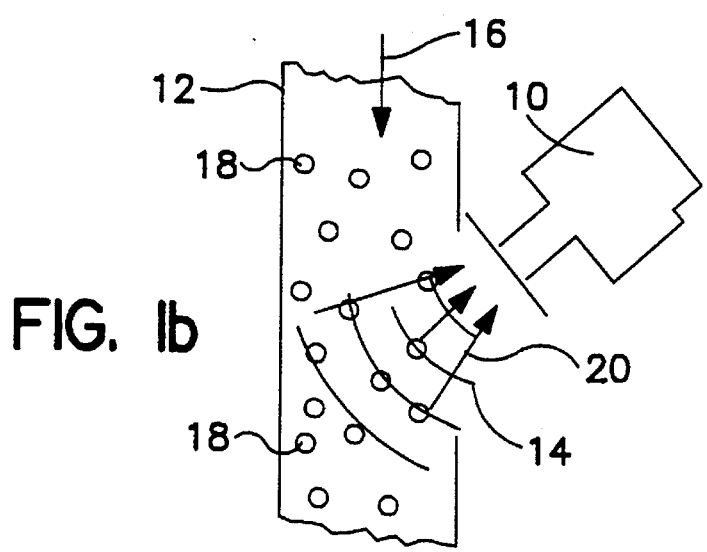
Figure 1C:
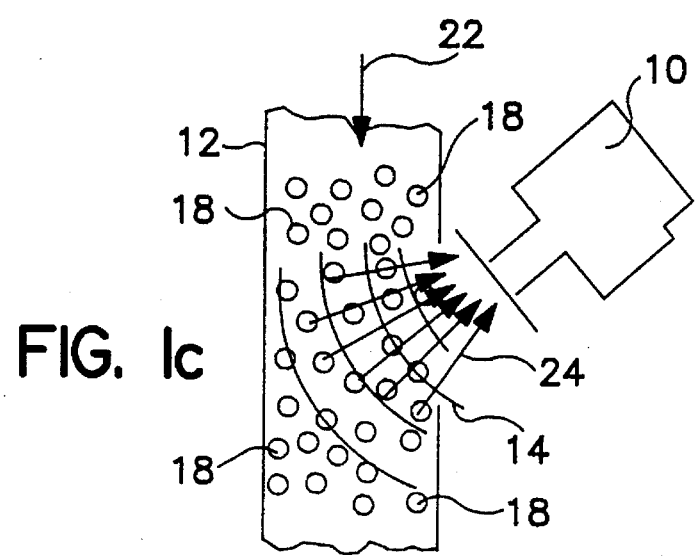

FIG. 1a shows a mass flow rate meter 10 of the present invention mounted adjacent a material flow path 12. Meter 10 is mounted outside of flow path 12 so that no material flowing through flow path 12 contacts meter 10. A transceiver (not shown) of meter 10 transmits electromagnetic energy signals 14 of known power and frequency so as to generate a field across material flow path 12. FIG. 1b shows process flow 16 of material 18 moving along flow path 12 and across the electromagnetic field established by signals 14. A first quantity of electromagnetic energy 20 is reflected by material 18. Electromagnetic energy 20 represents only the Doppler shifted energy (discussed below) reflected by moving material 18 and not any energy reflected by, for example, flow path 12. Only reflected energy 20 is important because the concentration of the material is related to this value. FIG. 1c shows a process flow 22 of material 18 moving along flow path 12 and across the electromagnetic field established by signals 14. A second quantity of electromagnetic energy 24 is reflected by material 18. Electromagnetic energy 24 also represents only the Doppler shifted energy reflected by the moving material 18. The magnitude of energy 24 is also related to the concentration of material 18. As can be seen by comparing FIGS. 1b and 1c, the concentration of material 18 is greater for process flow 22 in FIG. 1c than for process flow 16 in FIG. 1b. As can also be seen by comparing FIGS. 1b and 1c, this greater concentration results in second quantity of electromagnetic energy 24 being larger than first quantity of reflected electromagnetic energy 20.

The present invention further establishes that the flow rate of a material moving past a point can be determined by multiplying the mass of the material moving past that point by the velocity of the material. Mathematically, the relationship can be expressed as follows:

$$Q = \text{Mass} \times V$$

where

Q=Material flow rate

Mass=The quantity or amount of material

V=The material velocity The mass of the material can be determined based upon the volume of air and material illuminated by a transmitted electromagnetic energy signal divided by the concentration of the material. Mathematically, the relationship can be expressed as follows:

$$\text{Mass} = \frac{Vol.}{C}$$

where

Mass=The quantity or amount of material

Vol.=The volume of air and material illuminated by an electromagnetic energy signal C=The concentration of material The two immediately preceding equations can be combined to derive the following relationship:

$$Q = \frac{Vol. \times V}{C}$$

As discussed above, the concentration of a moving material is related to, and can be determined from, the magnitude of electromagnetic energy reflected by the moving material as it passes through a field of electromagnetic energy. For a given process flow, the volume of air and material illuminated by an electromagnetic energy signal is constant although the ratio of each that combine to define the volume may change.

When electromagnetic energy is reflected by a moving target or material, a shift in the frequency of electromagnetic energy reflected from the moving target or material occurs. This change in frequency is referred to as a Doppler shift. The magnitude of the frequency shift is proportional to the velocity of the material. Doppler shift frequency is mathematically expressed as:

$$F = 2V(f/c) \times \cos(theta)$$

where

F=The Doppler shift frequency

V=The material velocity f=The transmitted frequency of the electromagnetic signal c=The speed of light theta (θ)=The angle between the transmitted electromagnetic energy signal and the flow path of the material.

The above equation can be algebraically manipulated to solve for the material velocity. The resulting equation is:

$$V = \frac{F}{2(f/c) \times \cos(theta)}$$

The above equations can be algebraically combined to derive the following relationship:

$$Q = \frac{Vol \times F/[2(f/c) \times \cos(theta)]}{C}$$

This relationship is used by the present invention to determine the mass flow rate of a material through a process flow.

Figure 2:
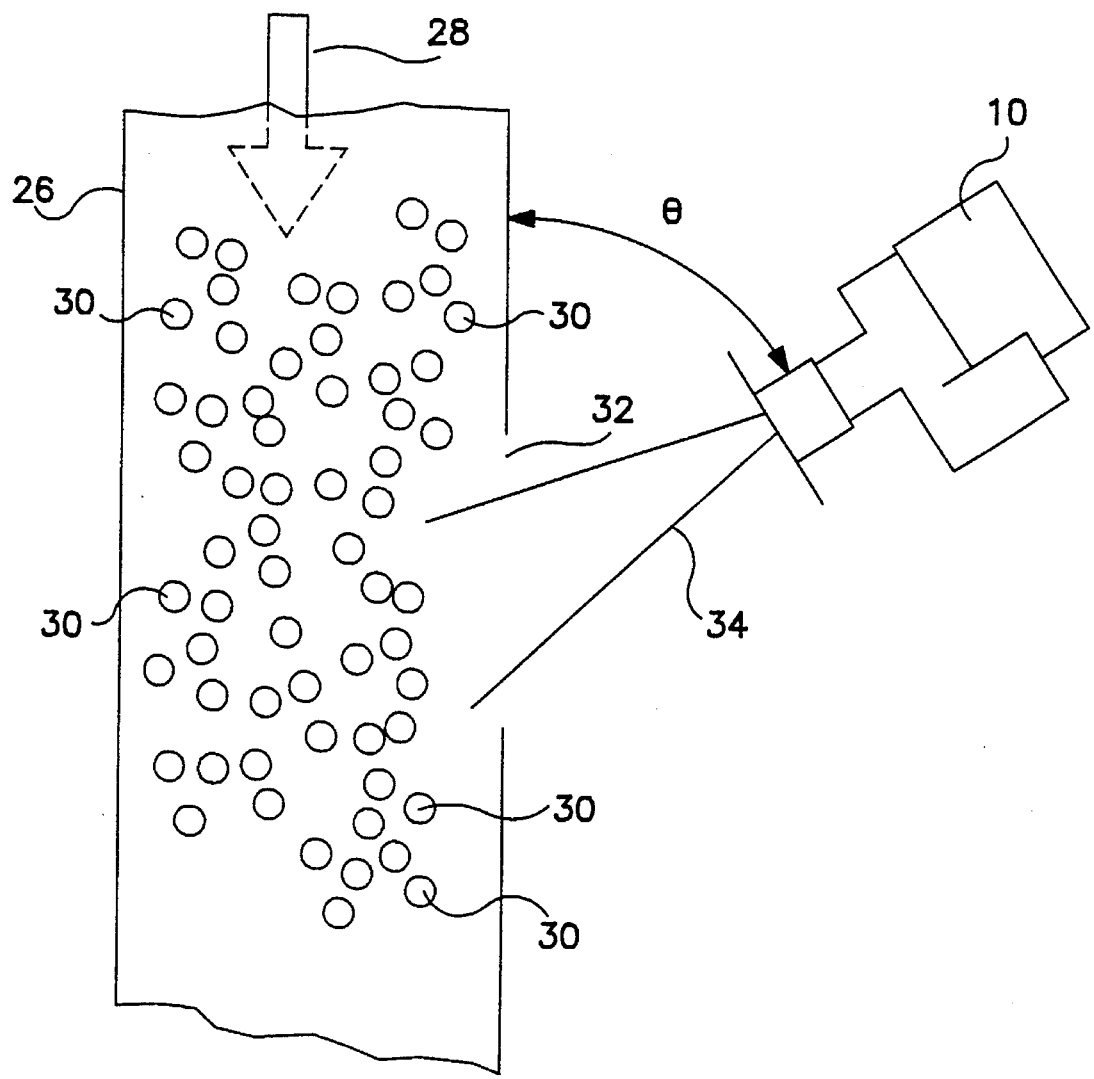
FIG. 2 illustrates a preferred setup for the meter of the present invention adjacent a material flow path.

FIG. 2 shows meter 10 of the present invention mounted adjacent a material flow path 26 through which a process flow 28 of material 30 moves. Material flow path 26 includes a window 32 through which transmitted electromagnetic signal 34 passes to illuminate a portion of moving material 30. Window 32 must have a non-conductive surface in order for signal 34 to penetrate it and illuminate material 30. Suitable materials for window 32 include non-leaded glass and plastic. Window 32 may also be an opening in flow path 26 as shown in FIG. 2.

Meter 10 is preferably mounted adjacent flow path 26 so as to maximize the amount of Doppler shift. This is achieved by mounting meter 10 at an angle theta (θ), discussed above and shown in FIG. 2, with respect to flow path 26. The preferred number of degrees for the angle θ has been determined to lie in the range of approximately 25 to 45 degrees.

Figure 3:
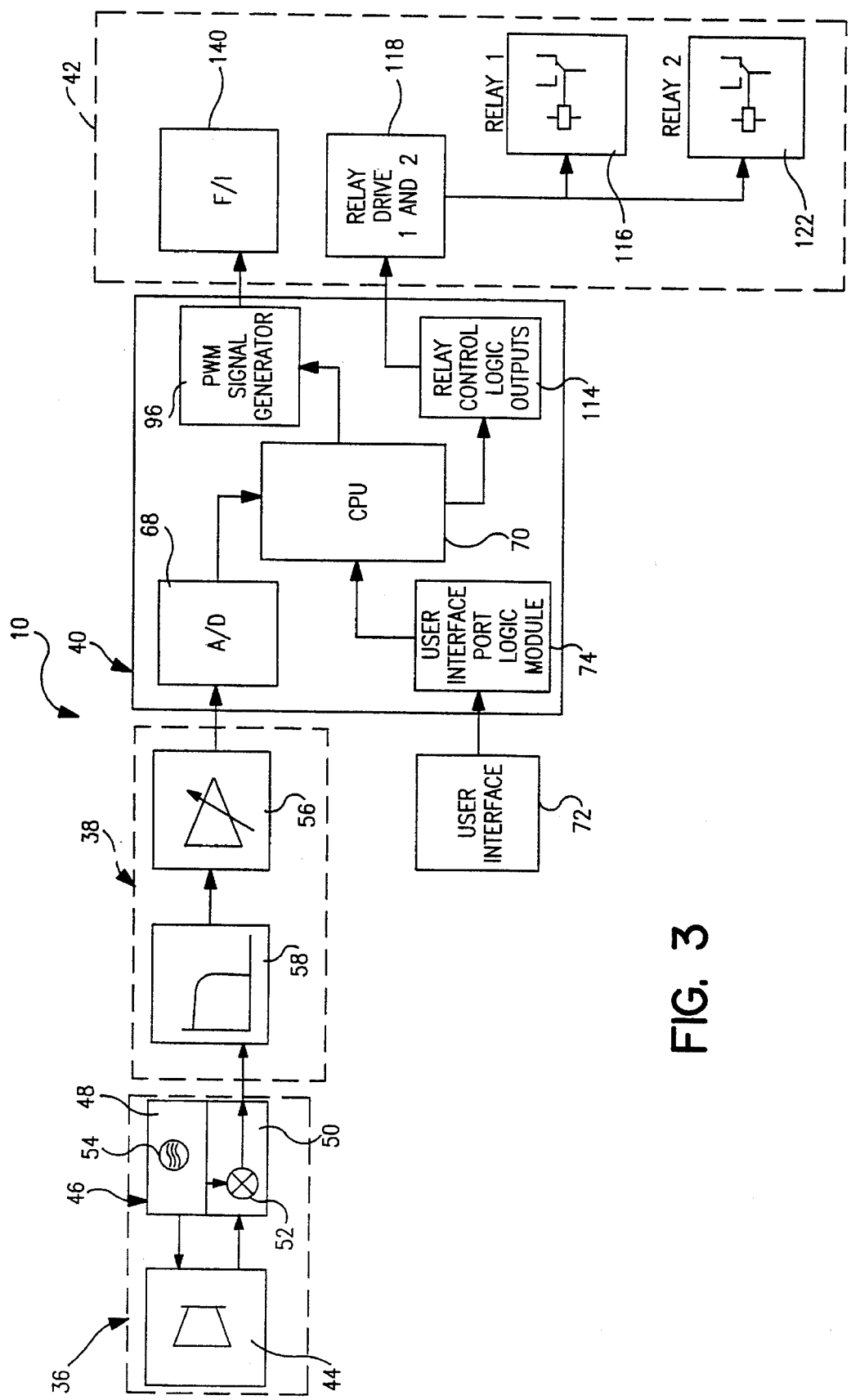
FIG. 3 is a block diagram of a preferred embodiment of the electrical circuitry of the mass flow rate meter of the present invention.

FIG. 3 is a block diagram of a preferred embodiment of the mass flow rate meter 10 of the present invention. Meter 10 includes a transceiver stage 36, an amplifier stage 38, a central processing unit stage 40, and an output stage 42.

Transceiver stage 36 includes an antenna 44 and a transceiver 46. Transceiver 46 transmits an electromagnetic energy signal of known power and frequency via antenna 44 to create a field of electromagnetic energy across a material flow path through which the material passes. Antenna 44 also detects and transmits electromagnetic energy signals reflected from target material passing through the field to transceiver 46. Transceiver 46 processes this reflected signal along with the Doppler shift in frequencies between the transmitted and reflected electromagnetic energy signals and outputs a signal having a magnitude directly proportional to the magnitude of the reflected electromagnetic energy signal and a frequency substantially equal to the difference between the frequency of the transmitted and reflected electromagnetic signals. This output signal is commonly known in the art as the "difference output signal." The magnitude of this signal is in the micro- to millivolt range.

Transceiver 46 can be made from discrete elements including a transmitter, generally indicated by block 48, a receiver, generally indicated by block 50, and a mixer 52. Transmitter 46 transmits an electromagnetic signal of a known frequency and power via antenna 44. The frequency of this signal is controlled by oscillator 54. Receiver 50 uses antenna 44 to receive the electromagnetic signals reflected by the moving material and output a signal proportional to the magnitude of these signals. Receiver 50 may include a transducer for this purpose. Mixer 52 combines the transmitted and reflected signals to generate a difference output signal having the characteristics described above. In a preferred embodiment of transceiver stage 36, antenna 44 is a 16 dB gain horn K band antenna and transceiver 46 is a Gunn Diode transceiver manufactured by Alpha Industries under model number GOS2870. Use of antennas with higher gain than 16 dB is appropriate where greater sensitivity is required.

Amplifier stage 38 filters and amplifies the difference output signal of transceiver 46 to an appropriate level so that the difference output signal can be processed by central processing unit stage 40. In a preferred embodiment, amplifier stage 38 produces an output signal in a range of between 0.5 to 6.0 volts (zero-to-peak) that lies within a frequency range of between approximately 0 to 15 kilohertz (kHz). Amplifier stage 38 includes low pass filter 58 with a nominal gain of approximately 30 decibels (dB) and a 3 dB roll-off point of approximately 15 kHz. Amplifier stage 38 further includes a multi-stage amplifier 56 with a combined gain of between approximately 4 dB and 29 dB and a bandwidth in excess of low pass filter 58.

Figure 4A:
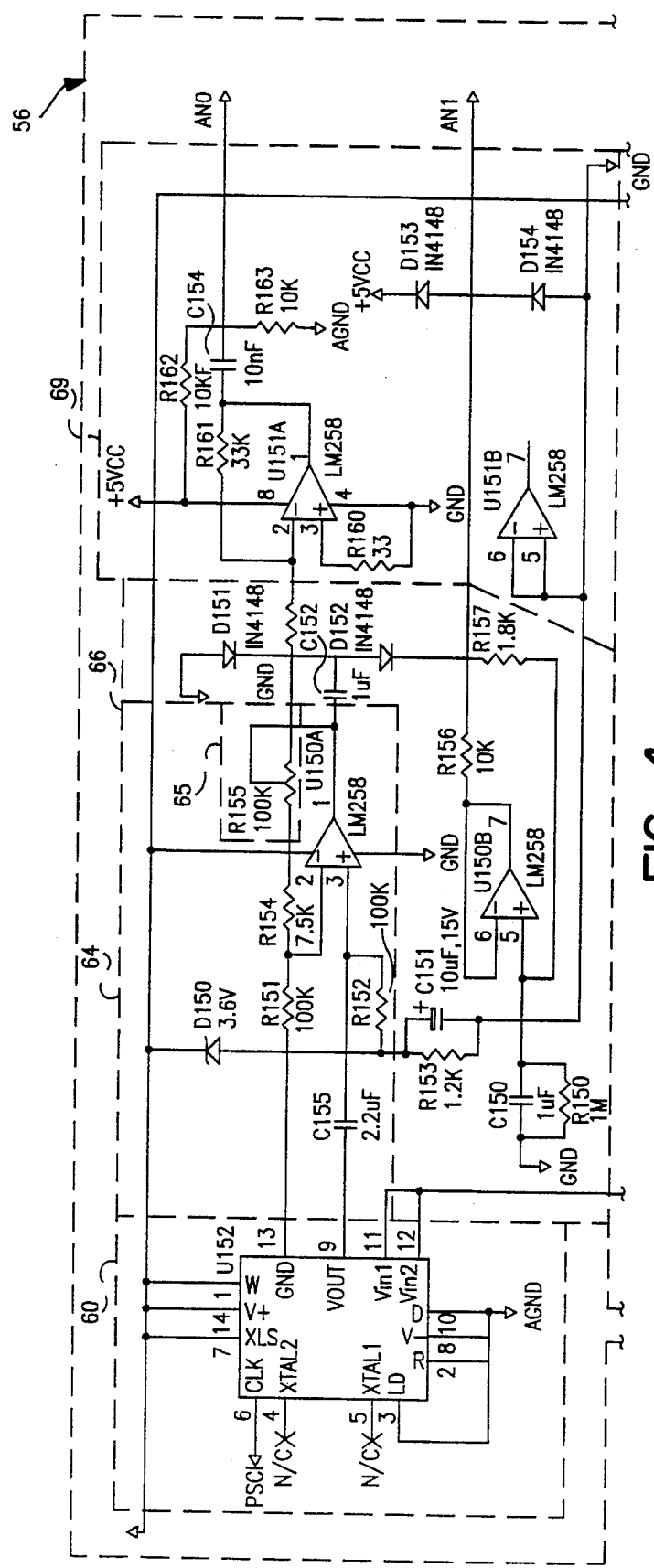
FIG. 4 is a circuit schematic of a preferred embodiment of a multi-stage amplifier and low pass filter of the present invention.
Figure 4B:
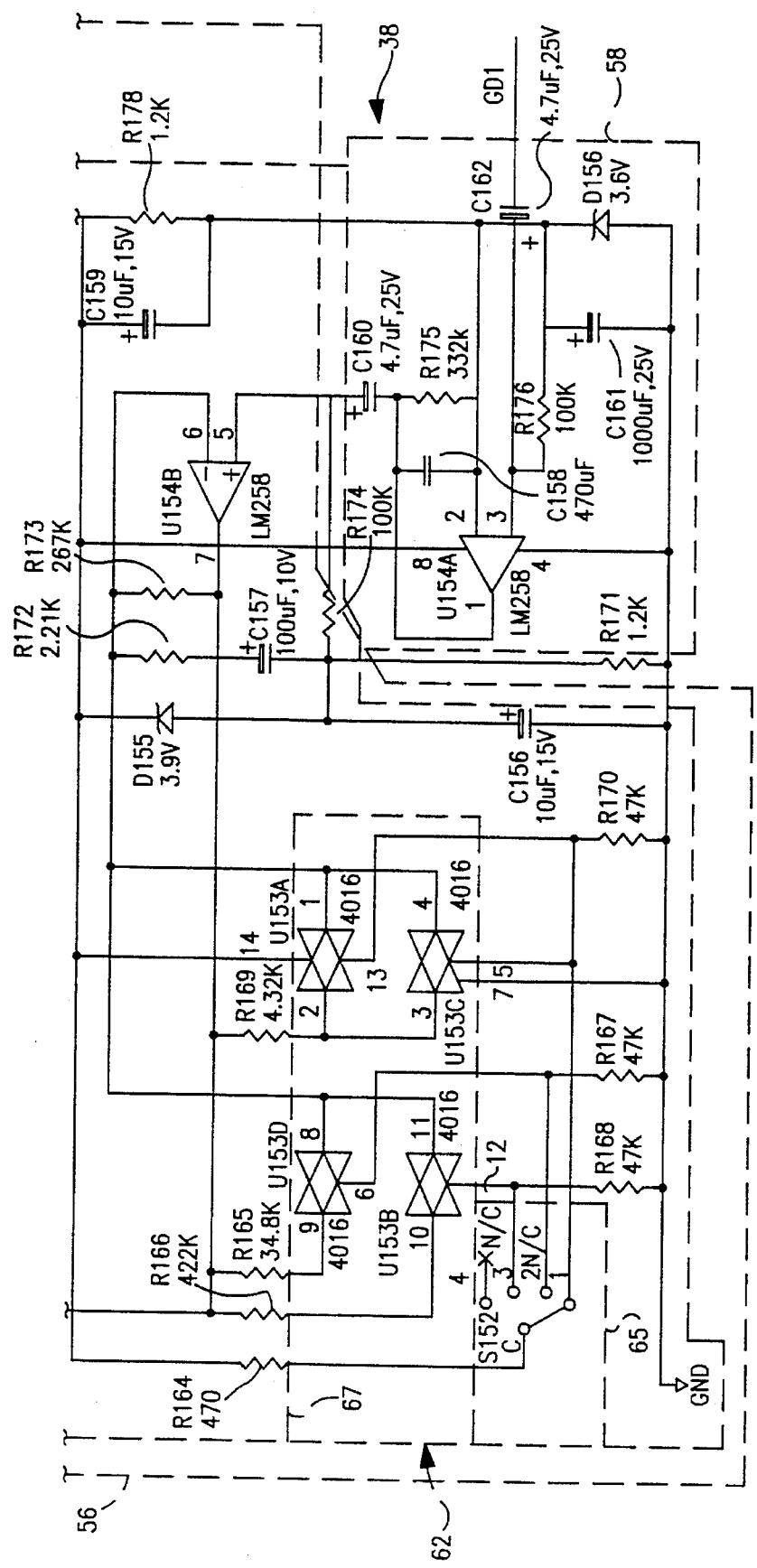

FIG. 4 shows a circuit schematic of a preferred embodiment of amplifier stage 38. Amplifier stage 38 includes a low pass filter 58 that receives the difference output signal of transceiver 46 on line GD1. Multistage amplifier 56 includes a user adjustable course gain amplifier 62 that provides a signal gain in a range of approximately 3 to 26 dB and is electrically connected to have a negative feedback. Manual switch 63 and analog switch 67 allow the value of feedback resistance used in amplifier 62 to be selectively changed. In the preferred embodiment illustrated, switch 67 is made by Motorola under model number MC14016. Amplifier 56 also includes a user adjustable fine gain amplifier 64 that provides a signal gain in a range of approximately 1 to 3 dB and is electrically connected to have a negative feedback. Potentiometer 65 allows the value of feedback resistance to be selectively changed through a range of resistance values. Multi-stage amplifier 56 further includes a 50/60 Hertz (Hz) notch filter 60 between amplifier 62 and amplifier 64 that attenuates residual power line noise. In the preferred embodiment illustrated, notch filter 60 is made by National Semiconductor under model number LMF90.

Signal rectifier 66 of multi-stage amplifier 56 converts the AC signal output of amplifier 64 to a dc signal. Rectifier 66 provides an easy means of deriving the magnitude of the output signal of amplifier 64 without having to use signal processing techniques and a central processing unit. The output of rectifier 66 for constant material velocities is inputted to central processing unit stage 40 via line AN1. For time-varying material velocities, the output of rectifier 66 is electrically connected to buffer circuit 69. Buffer output line AN0 is electrically connected to central processing unit stage 40.

As shown in FIG. 3, central processing unit stage 40 includes an analog-to-digital converter 68 that converts the amplified transceiver difference output signal on either line AN1 or AN0 into a digital format for use by central processing unit 70 (CPU). Central processing unit 70 calculates a linearized output signal representative of the flow rate of the material. Central processing unit 70 uses the digitized transceiver difference output signal and user supplied setup and calibration data to calculate this linearized signal. The user supplied setup and calibration data is provided via user interface 72 and user interface port logic module 74. User interface 72 of the present invention allows mass flow rate meter 10 to be calibrated based upon particular material process flow characteristics. User interface 72 also provides status information that allows a process flow to be monitored. User interface port logic module 74 connects user interface 72 to central processing unit 70.

Figure 5A:
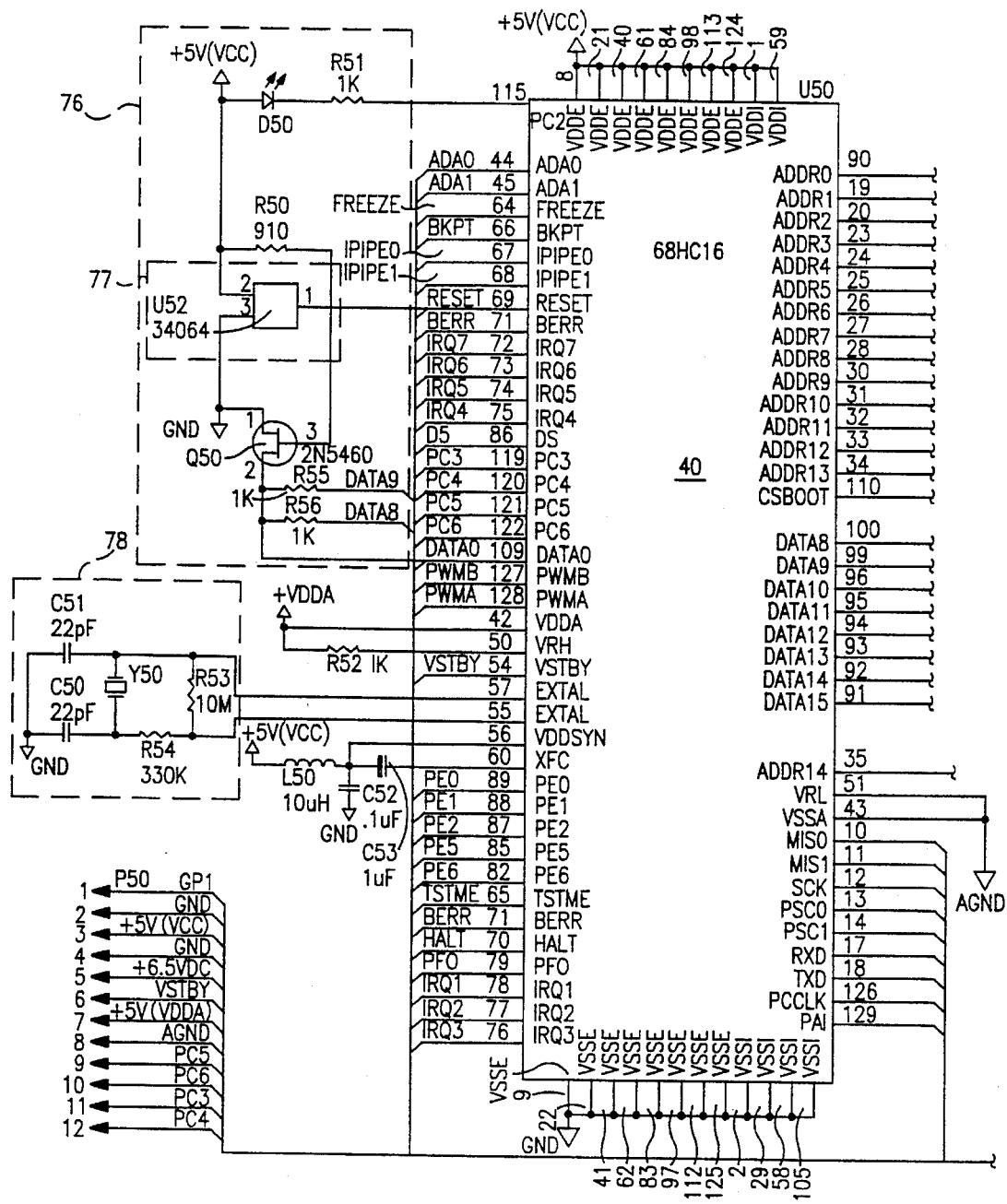
FIG. 5 is a circuit schematic of a preferred embodiment of a central processing unit stage of the present invention.
Figure 5B:
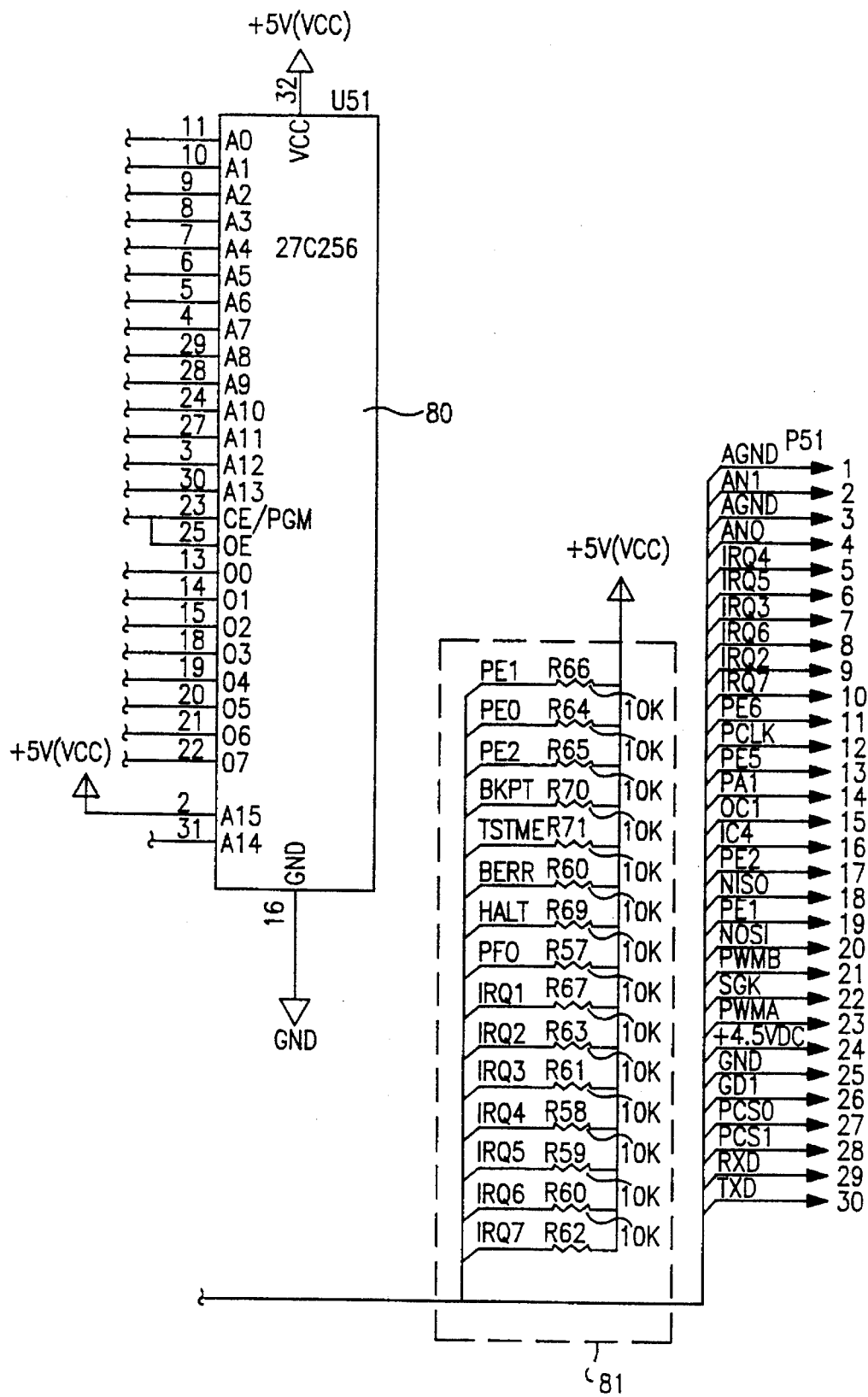

FIG. 5 shows a schematic of a preferred embodiment of central processing unit stage 40 which includes a Motorola MC68HC16Z1 programmable microcontroller. Although not shown in FIG. 5, this programmable microcontroller includes analog-to-digital converter 68, central processing unit 70, and user interface port logic module 74 as well as a pulse width modulated signal generator and relay control logic outputs discussed more fully below.

Central processing unit stage 40 of FIG. 5 also includes a power-up reset control 76 that provides a means to control a reset function of central processing unit 70 upon power up. Central processing unit stage 40 also includes a microcontroller power line reset chip 77. In the preferred embodiment illustrated in FIG. 5, chip 77 is an undervoltage detector made by Motorola under model number MC34064-5. A clock excitation circuit 78 provides a clocking signal for central processing unit 70 of stage 40. Program memory module 80 is an Erasable Programmable Read Only Memory (EPROM) that stores a software program for central processing unit stage 40 discussed more fully below. In the preferred embodiment illustrated in FIG. 5, module 80 is made by National Semiconductor under model number NM27C256. A resistor network 81 defines the configuration of central processing unit 70 after power up.

Figures 2, 6A:
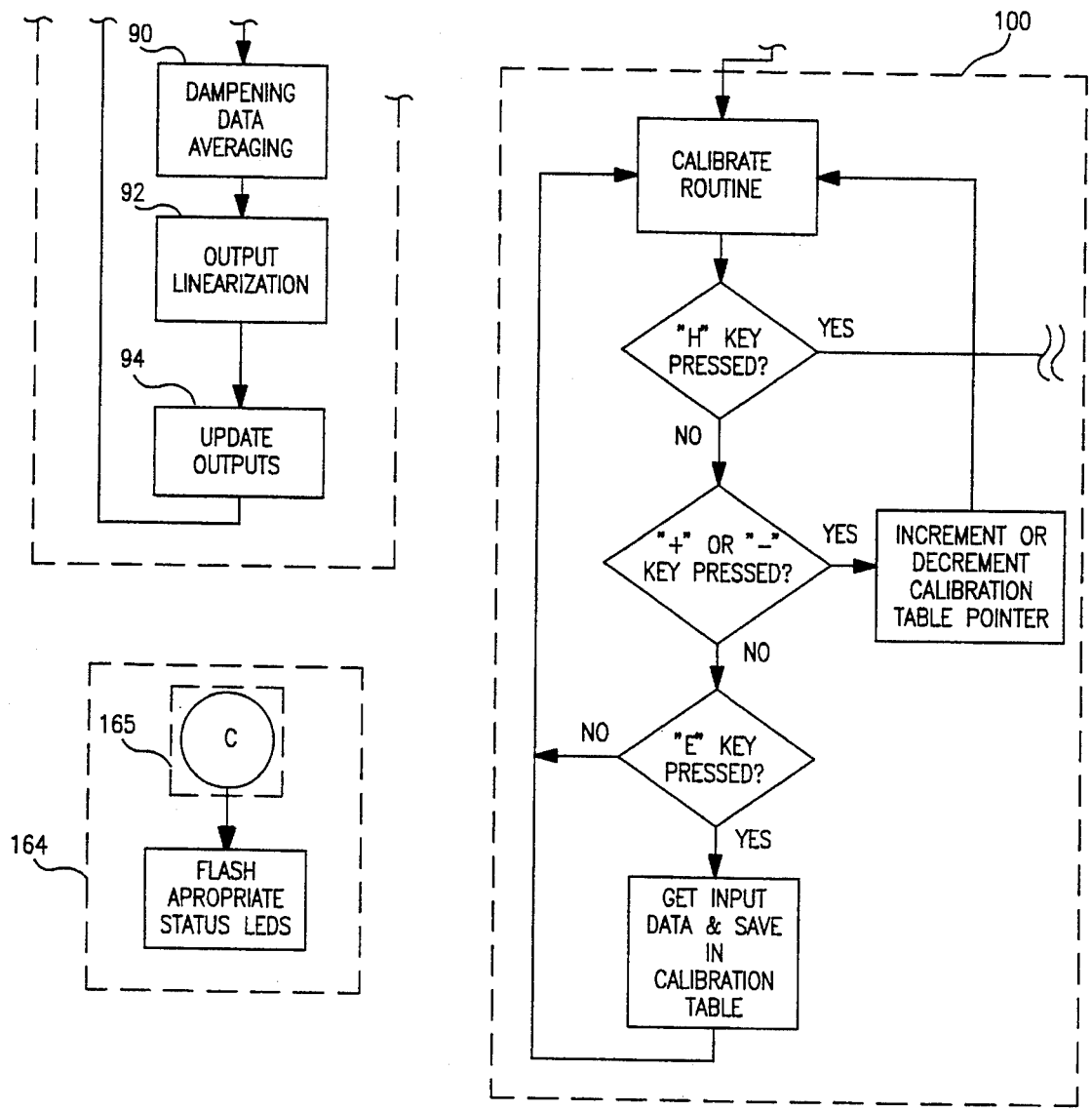
FIGS. 6a and 6b show a flow chart of a preferred embodiment of software of the present invention used to program and control a central processing unit stage of the present invention.
Figures 2, 6B:
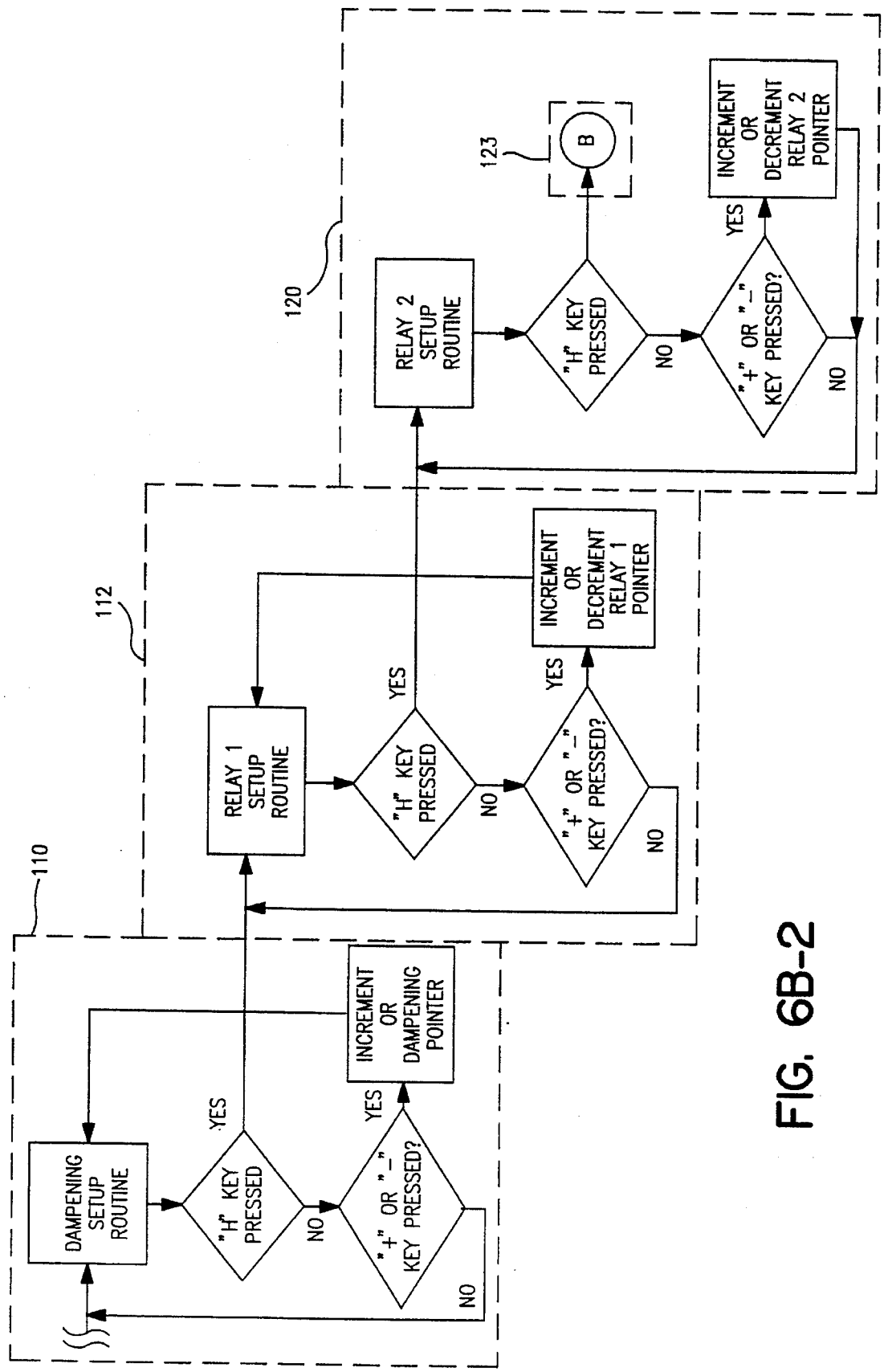

FIGS. 6a and 6b show a flow chart of a preferred embodiment of the software of the present invention used to program central processing unit 70 of stage 40 for accepting setup and calibration data from user interface 72 and digitized transceiver difference output signals to calculate a linearized signal representative of a material mass flow rate. An explanation of this software follows.

Upon power up, variables of central processing unit stage 40 are initialized to default settings unless already initialized. This is generally indicated by initialization routine 82 shown in FIG. 6a. The software next executes main program loop 84. Scan interface routine 86 within main program loop 84 scans user interface 72 to determine whether or not one or more of the setup and calibration variables is to be adjusted. This is determined by the pressing of a key on a keypad/control panel of user interface 72, labeled in preferred embodiments as the "H" key. FIGS. 7a–7d show a preferred embodiment of a keypad/control panel of user interface 72 which includes the "H" key. The setup, calibration, and adjustment of the unit via pressing of the "H" key and other keys on the keypad is discussed more fully below.

If the "H" key has not been pressed, the software next gathers an input data sample of the digitized transceiver difference output signal from A-to-D converter 68. This is generally indicated by Get Input Data routine 88 in FIG. 6a. This data is stored in a buffer of central processing unit 70 along with previous data samples. In preferred embodiments, this buffer is a First-In-First-Out (FIFO) buffer. The FIFO buffer stores a predetermined number of samples of data and discards the oldest sample when a new data sample is retrieved above the sample size of the buffer. The software next moves to a dampening/data averaging routine 90 which causes central processing unit 70 to average the data within the FIFO buffer. The software next moves to output linearization routine 92 which causes central processing unit 70 to linearize the average data by comparing it to data in a calibration table of central processing unit 70 which is generated during setup, calibration, and adjustment of unit 70 via user interface 72 as more fully discussed below. Output linearization routine 92 uses interpolation techniques to generate a linear approximation of the percentage of mass flow rate of material from zero to 100 percent by comparing the averaged value previously computed in routine 90 with the values of percentages of process flow stored in the calibration table.

An update outputs routine 94 of the software next causes central processing unit stage 40 to update output signals representative of the mass flow rate of material. In preferred embodiments, one of these output signals is a pulse width modulated signal that is created via pulse width modulated (pwm) signal generator 96 of central processing unit stage 40. The pulse width modulated signal is related to the percentage of mass flow rate of material flowing in a process flow as detected by meter 10 such that the larger the percentage, the wider the pulse width of the signal generated.

As discussed above, the software, central processing unit stage 40 and user interface 72 of the present invention allow mass flow rate meter 10 to be set up, calibrated, and adjusted based upon the particular characteristics of a material process flow. This setup, calibration, and adjustment is initiated by a user through pressing the "H" key on the keypad/control panel of user interface 72 shown in FIGS. 7a–7d. Pressing the "H" key one time branches from main program loop 84 to amplifier gain setting routine 98, as shown in the flow chart of FIG. 6a. Amplifier gain setting routine 98 allows the sensitivity of meter 10 to be adjusted to the ambient conditions of a particular material process flow. To adjust the amplification, the course adjustment and fine adjustment knobs of the keypad/control panel of user interface 72, shown in FIG. 7a, which correspond, respectively, to switch 63 and potentiometer 65 in FIG. 4, are adjusted until LED bar graph 73, also shown in FIG. 7a is lit to the appropriate value of maximum mass flow rate of a material process flow. This allows the sensitivity of meter 10 to be adjusted for that particular process flow so that optimum amplifier gain of meter 10 occurs during maximum mass flow rate of a material. For example, if the maximum material mass flow rate is 90%, course and fine adjustment knobs of the keypad of user interface 72 are adjusted until the LED bar graph reaches a value of 90% (i.e., 10 LEDs lit).

Pressing the "H" key two times from main program loop 84 or one time from amplifier gain setting routine 98 moves to calibrate routine 100 shown in FIG. 6a. Calibrate routine 100 allows calibration points to be set at various mass flow rates of material so that a calibration table can be set up to linearize, via interpolation techniques, the averaged transceiver difference output signal stored in the FIFO buffer of central processing unit 70. In preferred embodiments, up to 11 points can be stored in the calibration table of central processing unit 70. FIG. 7b shows the keypad/control panel of user interface 72 during execution of calibrate routine 100. To calibrate the unit, a zero calibration point (i.e., no process flow) should be entered first. To set this point, the material mass flow rate should be set to the lowest percentage of mass flow rate value to be measured. Once this flow rate is established, the "E" key is pressed once and the data point entered into the calibration table as the base or lowest value in the table. Additional calibration points are entered into the calibration table by pressing the "+" key, increasing the percentage of material mass flow rate from the minimum mass flow rate, and pressing the "E" key to enter that new data point. Previously entered data points can be changed by pressing the "−" key on the keypad of user interface 72 an appropriate number of times to arrive at that data point in the calibration table, changing the percentage of material mass flow rate, and then pressing the "E" key to enter that new data point in the calibration table. Calibrate routine 100 is exited by pressing the "H" key.

Pressing the "H" key three times from main program loop 84 or one time from calibrate routine 100 moves to dampening setup routine 110 shown in FIG. 6b. Dampening setup routine 110 allows the size of the FIFO buffer of central processing unit 70 to be increased or decreased by respectively pressing either the "+" or "−" keys on the keypad/control panel of user interface 72 as shown in FIG. 7c. Increasing the size of the FIFO buffer increases the number of digitized transceiver difference output signals that are averaged by central processing unit 70 during dampening/data average routine 90 before moving to output linearization routine 92. Output linearization routine 92 compares the average data derived in dampening/data average routine 90 to each value in the calibration table of the central processing unit 70, starting at the base or lowest value in the table. If, for example, the average data value is greater than that value stored at the base address but less than that value stored at the base address plus one, this means that the percentage of material flow is between the lowest and next highest percentage of material flow. Interpolation techniques are used by output linearization routine 92 to define the material mass flow rate to approximately one percent concentration increments.

Figure 8A:
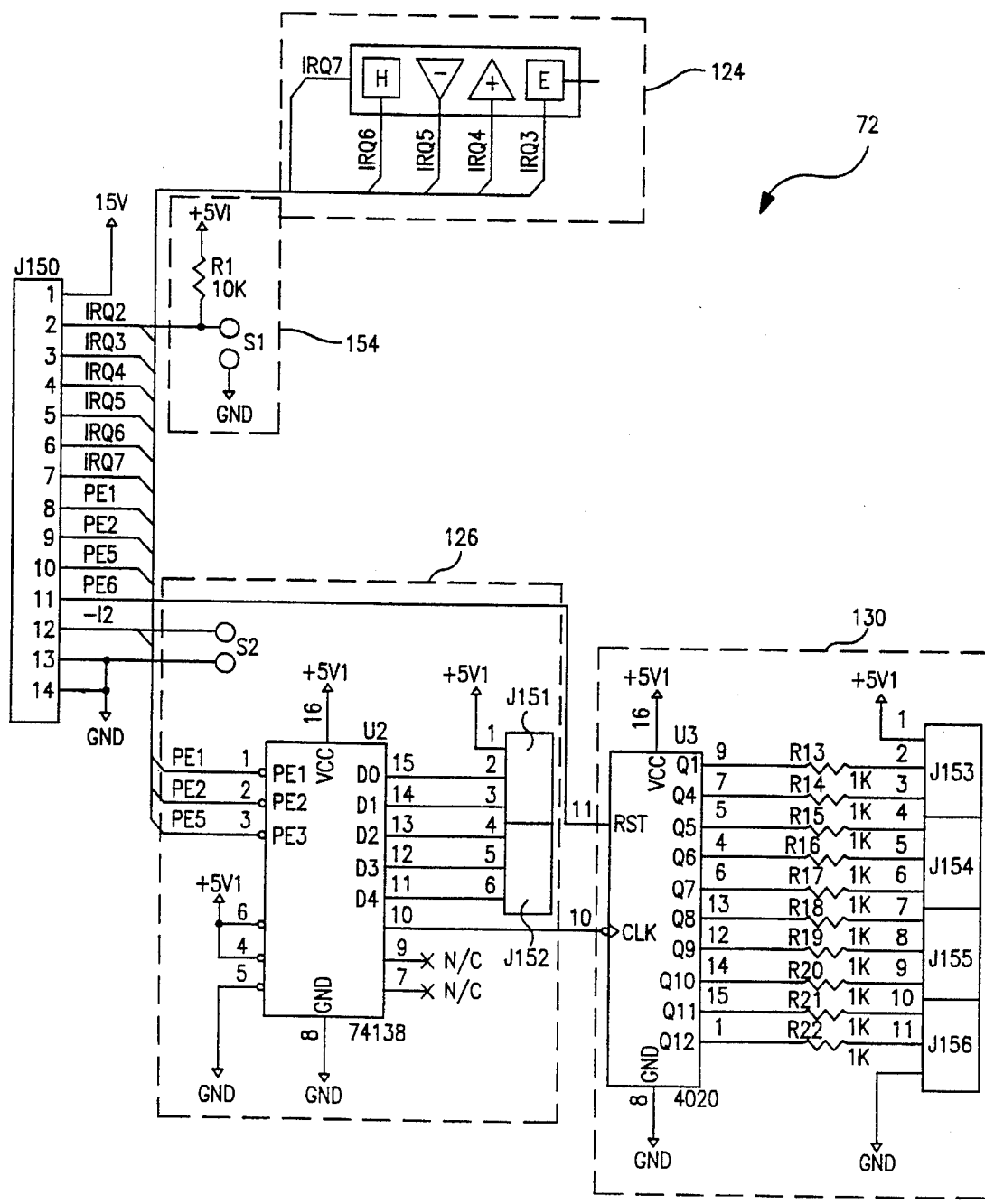
FIG. 8 is a circuit schematic of a preferred embodiment of the keypad/control panel of the user interface of the present invention.
Figure 8B:
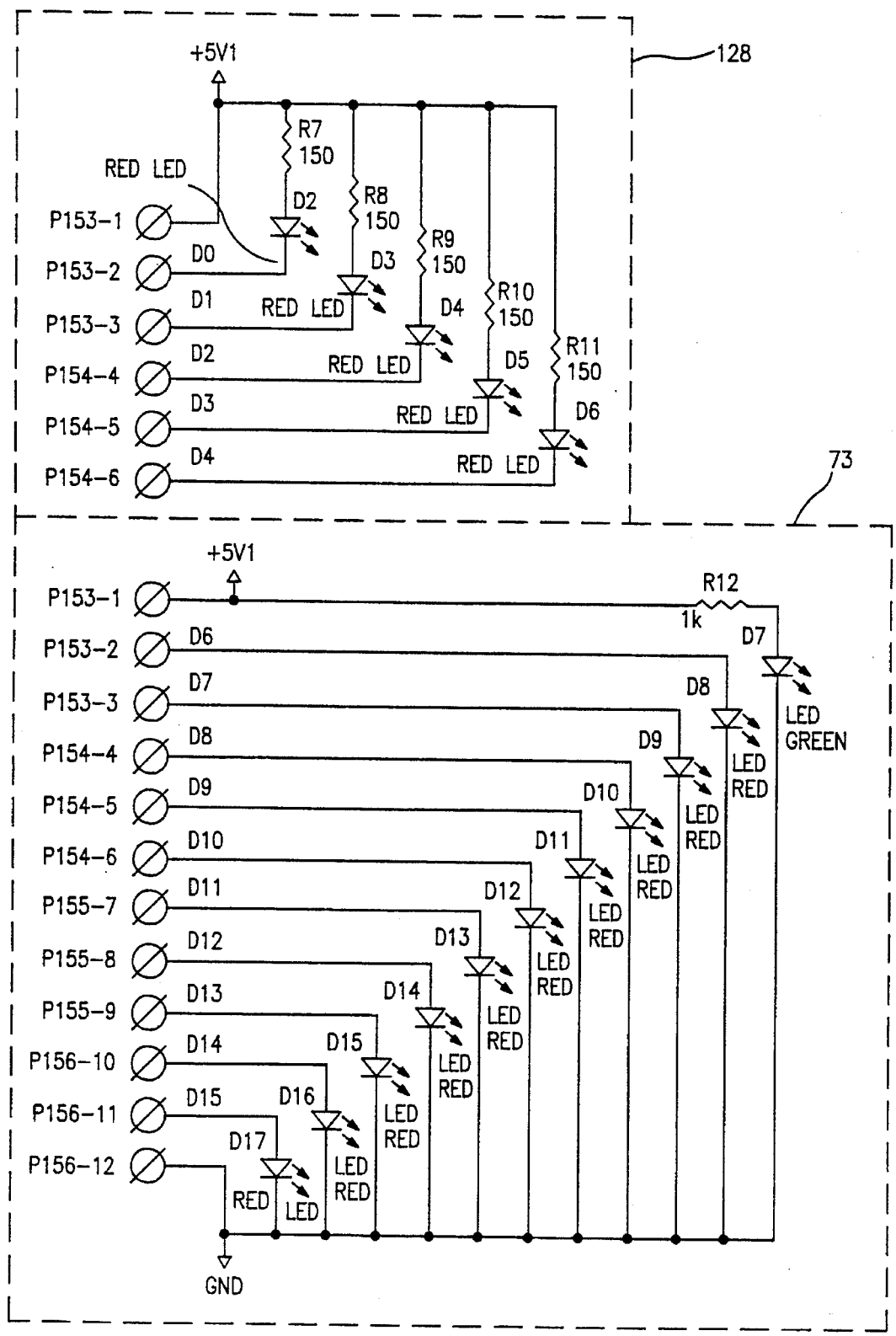

FIG. 8 shows a circuit schematic of a preferred embodiment of user interface 72. Keypad 124 having "H", "E", "+", and "−" keys for calibrating and adjusting meter 10, as discussed above is shown. Keypad 124 functions such that when a key is pressed, this forces a signal line at that key to a low level. The low level of the key is then sensed by central processing unit stage 40 which polls keypad 124 on a periodic basis.

A status LED driver 126 and associated status LEDs 128 are also shown in FIG. 8. Status LEDs provide information to a user of meter 10 such as which routine is being executed. In this preferred embodiment, status LED driver 126 is a National 74HC138 address decoder. Status LED driver 126 is controlled by logic outputs from central processing unit stage 40 that configure driver 126 to turn on the appropriate status LEDs.

An LED bar graph driver 130 and associated LED bar graph 73 are further shown in FIG. 8. As discussed above, LED bar graph 73 provides a visual indication of the percentage of mass flow rate for a process flow. In this preferred embodiment, LED bar graph driver 130 is a Motorola MC4020 binary counter. LED bar graph driver 130 is controlled by one or more logic signals from central processing unit stage 40 that time driver 130 to drive an appropriate number of LEDs of LED bar graph 73.

Pressing the "H" key four times from main program loop 84 or one time from dampening setup routine 110 moves to relay 1 setup routine 112 of the software shown in FIG. 6b. Relay 1 setup routine 112 configures relay control logic outputs module 114 of central processing unit stage 40 to actuate relay 116 through relay drive 1 and 2 module 118 if the percent of mass flow rate of material is below a predetermined amount. Relay control logic outputs module 114 of central processing unit stage 40 is configured to this value by pressing the "+" or "−" key to the appropriate percentage indicated by the LED bar graph of the keypad/control panel of user interface 72, as shown in FIG. 7d. Once this percentage of mass flow rate is set, the "H" key is pressed so that the software of the present invention moves to the relay 2 setup routine 120 shown in the flow chart of FIG. 6b. This routine configures relay control logic outputs module 114 of central processing unit stage 40 to activate relay 122 when the mass flow rate of material is at or above a predetermined value. This percentage of mass flow rate is set by pressing the "+" and "−" keys of the keypad of user interface 72 until the LED bar graph displays the appropriate percentage of material flow. The "H" key is then pressed to set this point and cause the software to branch back to main program loop 84 as indicated by branch "B" 123 in FIG. 6b.

Figure 9A:
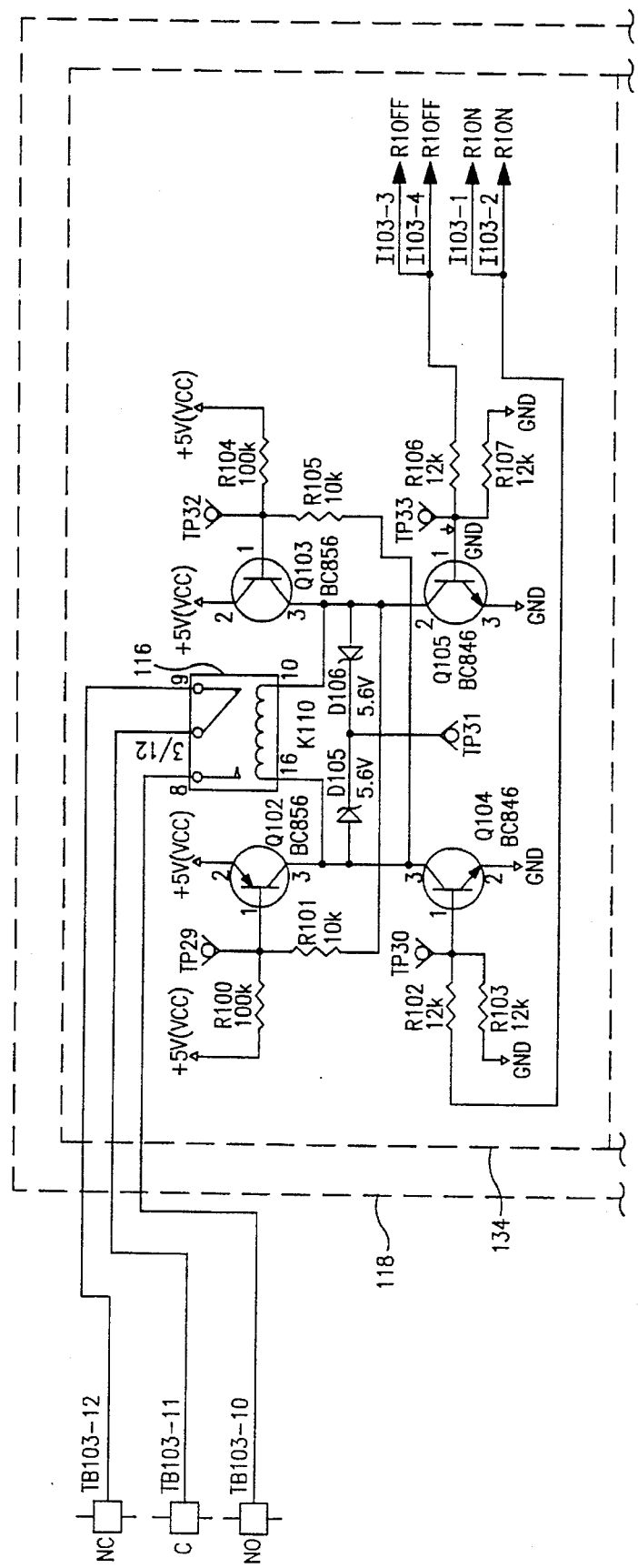
FIG. 9 is a schematic of a preferred embodiment of a circuit for controlling relay outputs of the mass flow meter of the present invention.
Figure 9B:
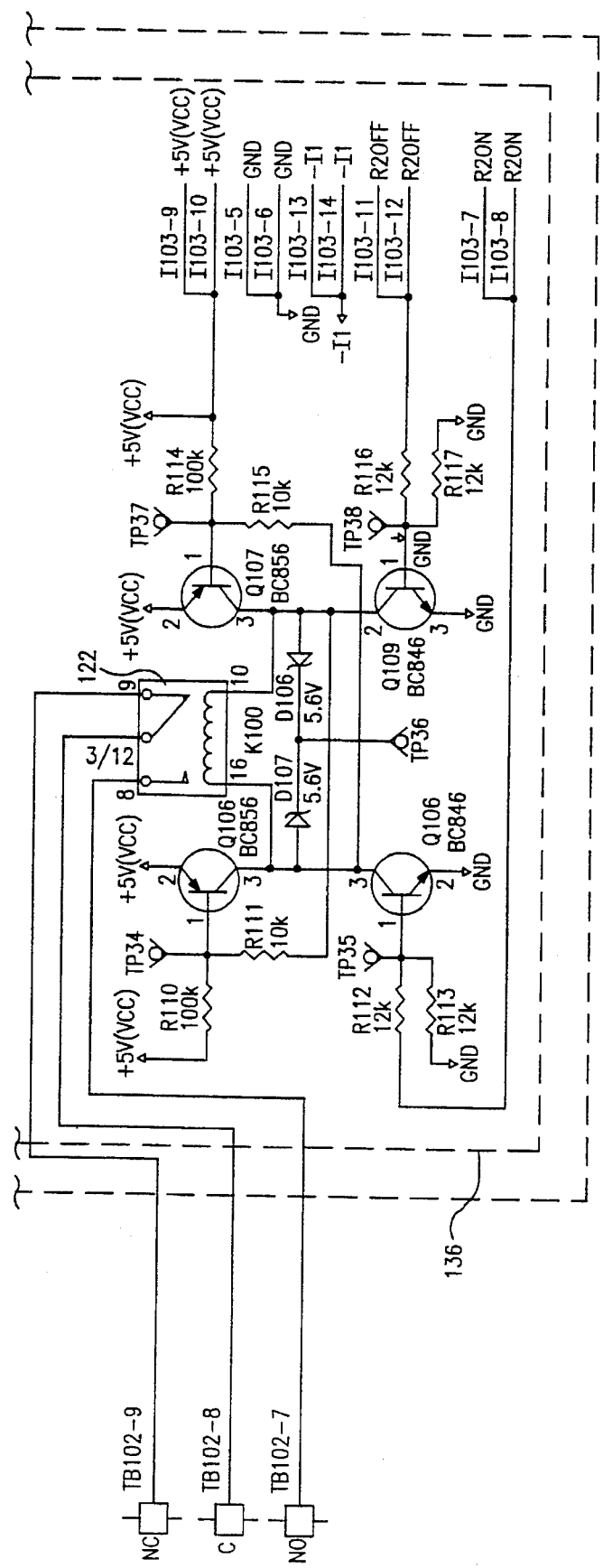

FIG. 9 shows a circuit schematic of a preferred embodiment of the above-described relay drive 1 and 2 module 118, relay 116, and relay 122. Relay drive 1 and 2 module 118 includes relay 1 driver 134 and relay 2 driver 136. As can be seen in FIG. 9, relay 1 driver 134 controls actuation of relay 116 and relay 2 driver 136 controls actuation of relay 122. As can also be seen in FIG. 9, both relay 1 driver 134 and relay 2 driver 136 use several transistors that energize and de-energize relays 116 and 122 based upon output signals from module 114.

The software used within central processing unit stage 40 allows one or more of the user calibrated features of the meter 10 to be readily changed. As shown in the flow chart of FIGS. 6a and 6b, the various routines of the software can be accessed by pressing the "H" key an appropriate number of times. For example, dampening setup routine 110 can be accessed from the main program loop 84 by pressing the "H" key three times. Main program loop 84 is returned to from dampening setup routine 110 by pressing the "H" key another three times.

The preferred embodiment of mass flow rate meter 10 further includes a frequency-to-current module 140 that generates an analog output current signal having a magnitude that is proportional to the pulse width of the output signal of generator 96. The magnitude of this output current signal increases as the width of the pulse increases. In a preferred embodiment of meter 10, frequency-to-current module 140 produces an output current signal having an industrial instrumentation magnitude range of between 4 to 20 milliamps (mA).

Figure 10A:
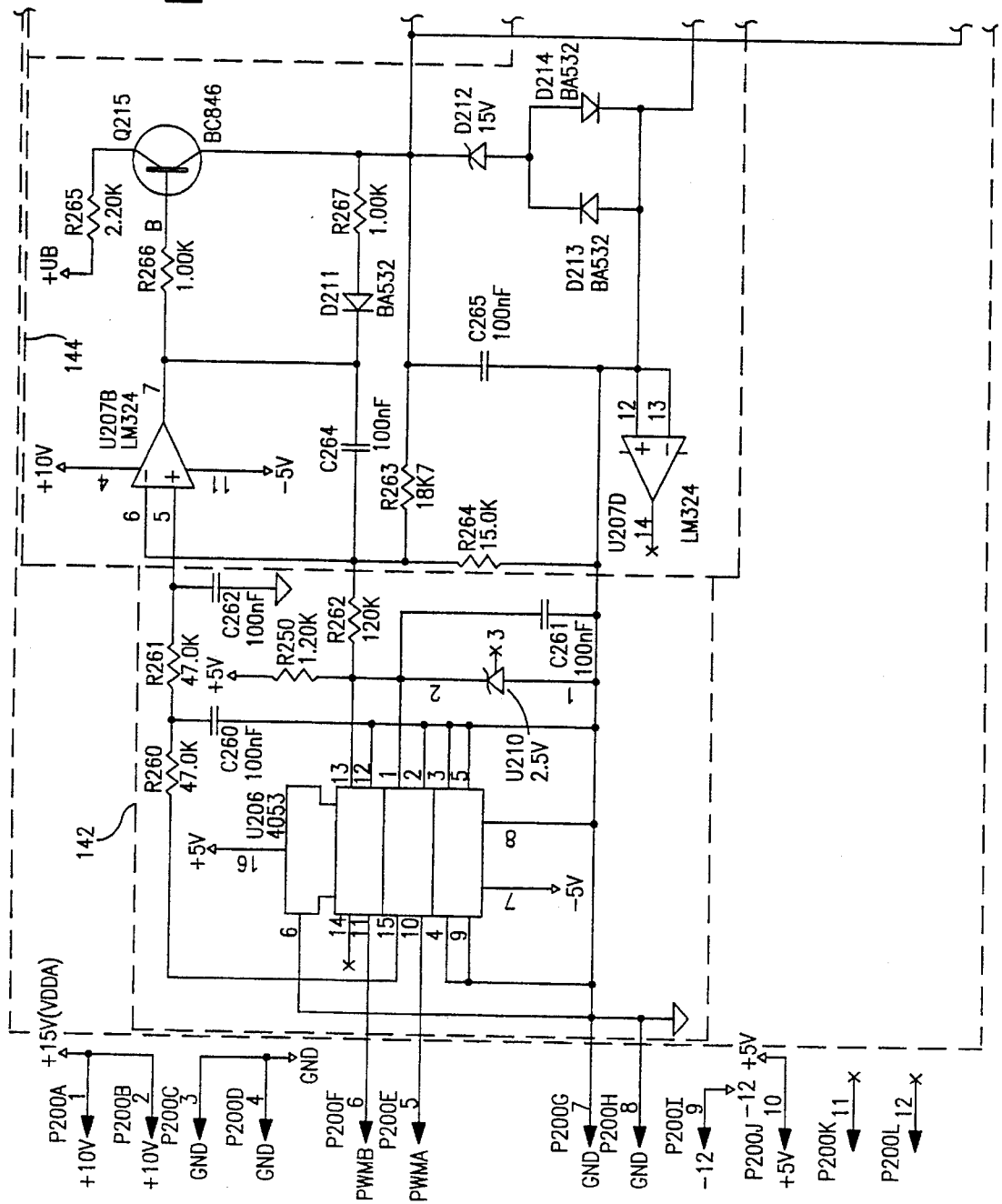
FIG. 10 is a circuit schematic of a preferred embodiment of an analog current output circuit of the mass flow rate meter of the present invention.
Figure 10B:
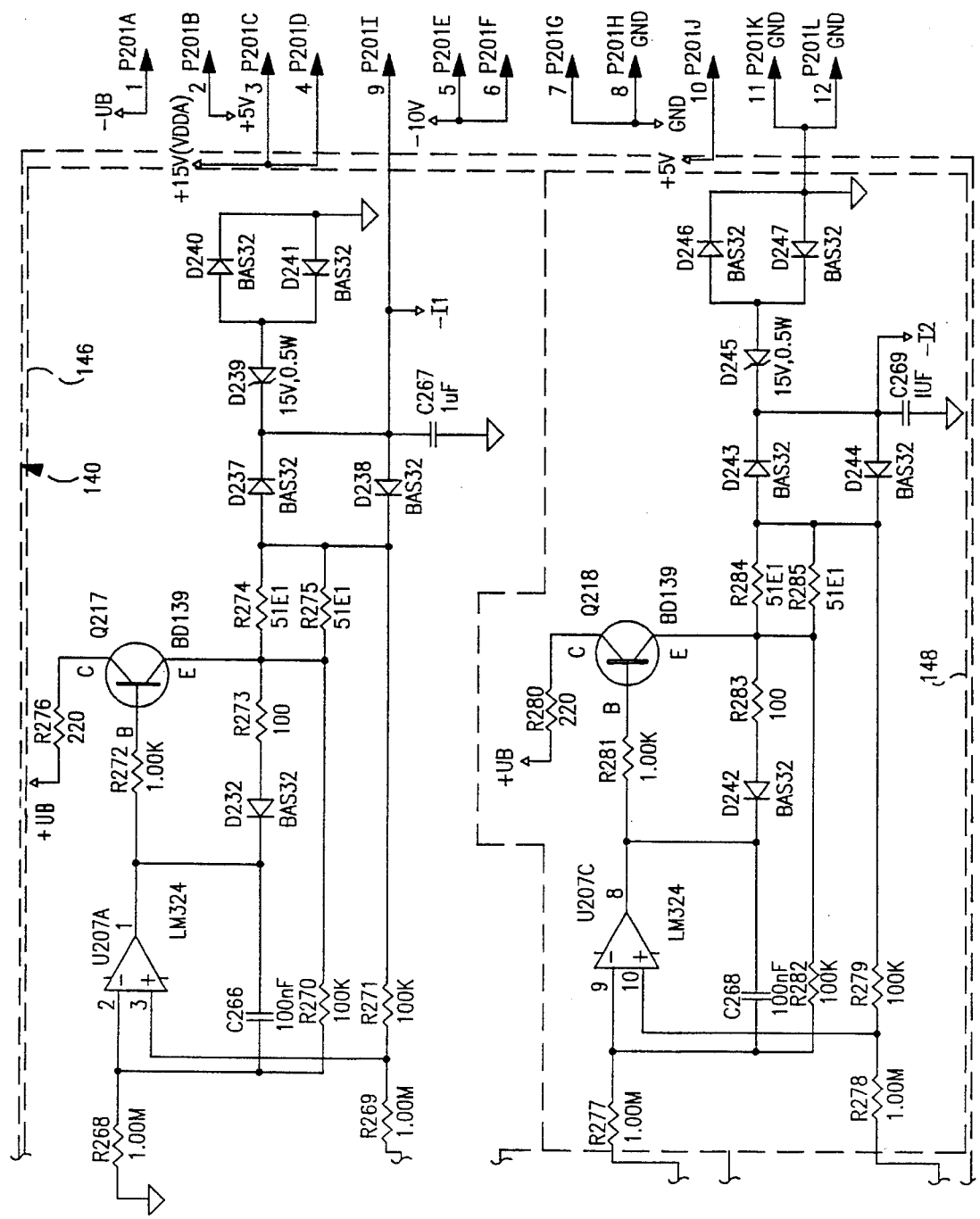

FIG. 10 shows a preferred embodiment of a circuit schematic of frequency-to-current module 140. Frequency-to-current module 140 includes a signal integrator 142 that converts the digital pulse width modulated signal of generator 96 into an analog signal. In the preferred embodiment illustrated in FIG. 10, signal integrator 142 is a National Semiconductor analog switch/demultiplexor designated by model number CD4053. Frequency-to-current module 140 also includes an integrator amplifier 144 that amplifies the analog output signal of signal integrator 142 to provide a larger output voltage range for greater signal resolution. Integrator amplifier 144 uses negative feedback to an operational amplifier to control the output voltage.

Frequency-to-current module 140 further includes voltage-to-current converter modules 146 and 148 that convert the voltage of amplifier 144 to a current in a substantially linear range of between 4 mA and 20 mA. In the preferred embodiment illustrated in FIG. 10, module 146 is electrically connected to user interface 72 and module 148 allows for electrical connection by equipment external from meter 10.

The software of the present invention also allows the analog current output generated by frequency-to-current module 140 to be calibrated and central processing unit 70 initialized with default variables. Such calibration and initialization is initiated by inserting a jumper at jumper connection point 154 in the schematic of FIG. 8. The software recognizes the insertion of this jumper as shown by user selected matrix line 1? module 156 in FIG. 6a and associated branch "A" 157.

After moving to "A" 157, the software executes variable default setting routine 158, shown in FIG. 6b, where relay 1 and relay 2 switch points, the damping value, and the calibration values of meter 10 are reset to default values stored in memory module 80 upon the pressing of the "E" key. In a preferred embodiment of meter 10, relay 1 switch point is set to 30%, relay 2 switch point is set to 70%, the dampening value is set to 2 seconds, and the calibration table values are set so that the base location value is 40 hexidecimal, the next nine location values are reset to zero, and the eleventh or highest location value is set to a value of F8 hexidecimal.

Pressing the "H" one time branches to 4 mA output adjustment routine 160 shown in FIG. 6b. Routine 160 can be accessed without resetting the variables or after reset. Central processing unit stage 40 generates specific hexidecimal numbers that represent the 4 mA and 20 mA current outputs. The 4 mA output adjustment routine 160 allows the hexidecimal numbers that represent the 4 mA output to be adjusted to accommodate for variations in circuitry performance from one meter 10 to another meter 10. The hexidecimal number representing the 4 mA current output is adjusted respectively upwardly or downwardly by pressing the "+" or "−" key. This allows output current adjustment to be made via software which is more convenient and less costly than making adjustments at a circuit level to compensate for performance differences from meter to meter.

Pressing the "H" one time from routine 160 or two times from routine 158 branches to 20 mA output adjustment routine 162 shown in FIG. 6b. The hexidecimal number representing the 20 mA current output is adjusted respectively upwardly or downwardly by pressing the "+" or "−" key.

Main program loop 84 is returned to by pressing the "H" one time from routine 162, two times from routine 160, and three times from routine 158. This is generally indicated by branch "B" 123 in FIGS. 6a and 6b.

The software directs central processing unit 70 to flash appropriate LEDs on user interface 72 at appropriate intervals as indicated by flash appropriate status LEDs routine 164 and branch "C" 165 in FIG. 6a. Branch "C" can occur during main program loop 84 or routines such as amplifier gain setting routine 98. After flashing appropriate LEDs on user interface 72 via execution of routine 164, the software branches back to where the initial branch "C" 165 took place and continues execution from that point. In preferred embodiments, branch "C" 165 and routine 164 are implemented by a periodic interrupt timer that directs the software to execute branch "C" 165 and routine 164 at the expiration of a time interval defined in the periodic interrupt timer.

From the preceding description of the preferred embodiments, it is evident that the objects of the invention are attained. Although the invention has been described and illustrated in detail, it is to be clearly understood that the same is intended by way of illustration and example only and is not to be taken by way of limitation. The spirit and scope of the invention are to be limited only by the terms of the appended claims.

What is claimed is:

1. An apparatus for measuring the mass flow rate of a material moving along a flow path at an assumed velocity, the apparatus comprising:

a source that generates a field of electromagnetic energy through which a material moving along a flow path passes;

a receiver that receives an amount of electromagnetic energy reflected from the material which is proportional to the concentration of material moving along the flow path; and means for processing the amount of electromagnetic energy reflected from the material passing through the field and the assumed velocity to generate a signal representing a mass flow rate of the material.

2. The apparatus of claim 1, wherein the response is linear for a range of magnitudes of reflected electromagnetic energies.

3. The apparatus of claim 1, wherein the response is a voltage proportional to the flow rate of the material.

4. The apparatus of claim 1, wherein the field of electromagnetic energy has a frequency in a microwave range.

5. The apparatus of claim 1, wherein the field of electromagnetic energy is positioned at a fixed location along the flow path of the material.

6. The apparatus of claim 5, wherein the material is in free fall such that a velocity of the material is dependent upon the position of the material along the flow path.

7. The apparatus of claim 1, further comprising means for detecting a change in frequency between the field of electromagnetic energy and the electromagnetic energy reflected from the material passing through the field to generate, in conjunction with the processing means, a response related to the flow rate of the material when a velocity of the material is time varying.

8. The apparatus of claim 7, wherein the response is linear for a range of reflected electromagnetic energies.

9. The apparatus of claim 1, further comprising means for determining a value for the assumed velocity of the material moving along the flow path.

10. A meter for measuring a mass flow rate of a material moving along a flow path at an assumed velocity, the meter comprising:

means positioned along the flow path of the moving material for transmitting electromagnetic energy of a characterized magnitude and frequency to illuminate a predetermined quantity of moving material;

means for detecting an amount of energy reflected from the illuminated quantity of moving material which is proportional to the concentration of material moving along the flow path; and means associated with the detecting means for converting the amount of reflected energy and the assumed velocity to a response related to the mass flow rate of the material.

11. The meter of claim 10 wherein the magnitude of the reflected energy is dependent upon a concentration of the material and the response is linear for a range of material concentrations.

12. The meter of claim 10, wherein the transmitted electromagnetic energy has a microwave frequency.

13. The meter of claim 10, wherein the transmitting and detecting means include an antenna and a transceiver.

14. The meter of claim 13, wherein an output of the transceiver is electrically connected to the converting means and a signal appears at the output that is related to the magnitude of the energy reflected by the material.

15. The meter of claim 10, wherein the converting means includes means for amplifying the signal appearing at the output of the transceiver.

16. The meter of claim 15, wherein the amplifying means has an adjustable gain and a generally flat magnitude response for a predetermined frequency range.

17. The meter of claim 16, wherein the predetermined frequency range is in an audio frequency range.

18. The meter of claim 15, wherein the converting means includes means having an input electrically connected to an output of the amplifying means for processing a signal appearing at the output of the amplifying means to provide first and second signals at respective first and second outputs of the processing means.

19. The meter of claim 18, further comprising means having an input electrically connected to the first output of the processing means for driving at least one relay.

20. The meter of claim 18, further comprising means having an input electrically connected to the second output of the processing means for generating a current output related to the second signal so that a larger second signal pulse width produces a larger current output.

21. The meter of claim 10, further comprising control means for configuring and calibrating the converting means to generate the response.

22. The meter of claim 10, further comprising means for determining a value for the assumed velocity of the material moving along the flow path.

23. The meter of claim 10, further comprising means for determining a value for the assumed velocity of the material moving along the flow path.

24. A meter for measuring a mass flow rate of a material moving along a flow path, the meter comprising an antenna positioned at a location along the flow path;

a transceiver electrically connected to the antenna, the transceiver transmitting, in conjunction with the antenna, a field of electromagnetic energy of known magnitude and frequency and receiving reflected electromagnetic energy from material crossing the field to produce a signal related to the magnitude of the reflected electromagnetic energy which is proportional to the concentration of material moving along the flow path;

an amplifier electrically connected to the transceiver and amplifying the signal produced by the transceiver;

a control unit enabling calibration for a particular material flow rate measurement; and a central processing unit electrically connected to the amplifier and control unit and generating at least one output signal based upon data received from the control unit and a signal received from the amplifier.

25. The meter of claim 24, wherein the antenna includes a 16 dB gain horn K band antenna.

26. The meter of claim 24, wherein the transceiver includes a gunn diode transceiver.

27. The meter of claim 24, wherein the amplifier has an adjustable gain and a generally flat magnitude response for a predetermined frequency range.

28. The meter of claim 27, wherein the response is generally flat from 0 to 15 kilo Hertz and ranges from 0.5 to 6.0 Volts zero to peak.

29. The meter of claim 24, wherein the control unit includes a manual entry interface.

30. The meter of claim 24, wherein the central processing unit generates a pulse width modulated output signal and further comprising means electrically associated with the pulse width modulated output signal for producing a current output related to the pulse width of the output signal so that a larger pulse width produces a larger current output.

31. The meter of claim 24, further comprising relay means electrically associated with the output signal of the central processing unit for opening and closing at least one relay based upon a magnitude of the central processing unit output signal.

32. A method of measuring the mass flow rate of a material moving along a flow path at an assumed velocity, comprising the steps of:

transmitting a field of electromagnetic energy of known magnitude and frequency across the flow path;

detecting the magnitude of electromagnetic energy reflected from material moving across the field which is proportional to the concentration of material moving along the flow path; and converting the magnitude of reflected energy and the assumed velocity to a response related to the mass flow rate of the material.

33. The method of claim 32, wherein the response is linear for a range of material densities.

34. The method of claim 32, further comprising the step of calibrating for a particular material flow.

35. The method of claim 32, wherein the transmitted electromagnetic energy has a microwave frequency.

* * * * *